United States Patent [19]

Sadoway

[11] Patent Number: 4,764,257
[45] Date of Patent: Aug. 16, 1988

[54] ALUMINUM REFERENCE ELECTRODE

[75] Inventor: Donald R. Sadoway, Belmont, Mass.

[73] Assignee: Massachusetts Institute of Technology, Cambridge, Mass.

[21] Appl. No.: 783,776

[22] Filed: Oct. 3, 1985

[51] Int. Cl.⁴ ............................................. G01N 27/46
[52] U.S. Cl. ..................................... 204/1 T; 204/67; 204/400; 204/435
[58] Field of Search ................. 204/1 T, 400, 435, 67

[56] References Cited

U.S. PATENT DOCUMENTS

| | | | |
|---|---|---|---|
| 3,281,348 | 10/1966 | Schmumacher et al. | 204/435 |
| 3,324,013 | 6/1967 | Dewing | 204/1 T |
| 3,335,076 | 8/1967 | Burkhardt | 204/67 |
| 3,471,390 | 10/1969 | Kibby et al. | 204/67 |
| 4,601,810 | 7/1986 | Tiwari et al. | 204/413 |
| 4,645,571 | 2/1987 | Dubreuil et al. | 204/435 |

OTHER PUBLICATIONS

*Aluminum Electrolysis–Fundamentals of the Hall-Heroult Process*, (2nd Ed.), K. Grjotheim et al, pp. 128–139, 184–215 (1982).
"Zur Elektrometallurgie Des Aluminiums", Paul Drobach, *Ztschr. Electrochem*, Bd. 42, Nr. 2 (1936), pp. 65–70.
"Aluminum/Cryolite Reference Electrodes for Use in Cryolite-Based Melts", John W. Burgman et al, *J. Electrochem. Soc.: Electrochemical Science and Technology*, pp. 496–500, Mar. 1986.
"Handbook of Chemistry & Physics", 55th ed., pp. B-63 & B-138.

*Primary Examiner*—T. Tung
*Attorney, Agent, or Firm*—Hamilton, Brook, Smith & Reynolds

[57] ABSTRACT

A stable reference electrode for use in monitoring and controlling the process of electrolytic reduction of a metal. In the case of Hall cell reduction of aluminum, the reference electrode comprises a pool of molten aluminum and a solution of molten cryolite, $Na_3AlF_6$, wherein the electrical connection to the molten aluminum does not contact the highly corrosive molten salt solution. This is accomplished by altering the density of either the aluminum (decreasing the density) or the electrolyte (increasing the density) so that the aluminum floats on top of the molten salt solution.

18 Claims, 1 Drawing Sheet

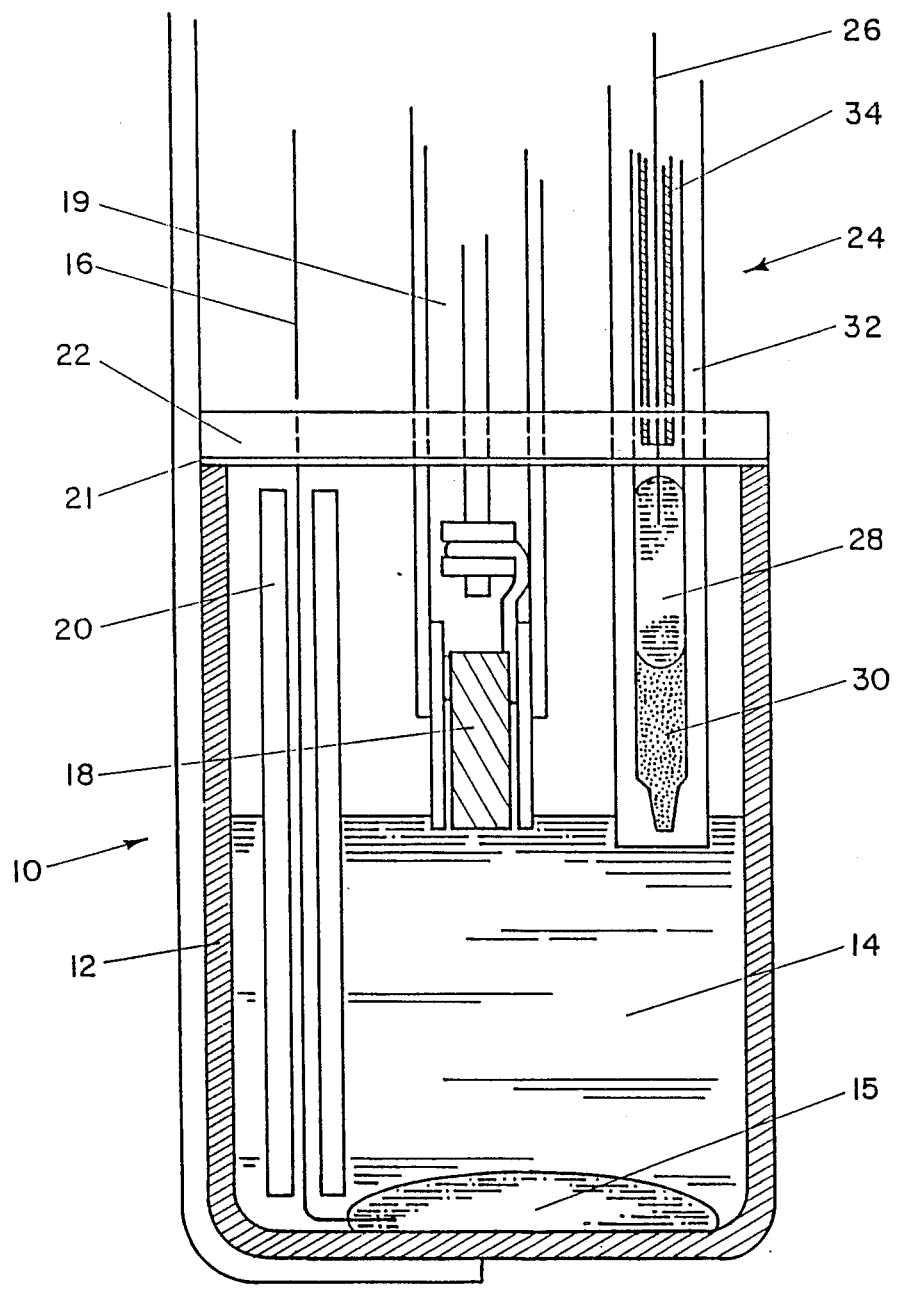

ALUMINUM REFERENCE ELECTRODE

The Government has certain rights in this invention by virtue of U.S. Department of Energy Grant No. DE-FG07-83-ID12380.

BACKGROUND OF THE INVENTION

This invention is generally in the field of reference electrodes and in particular the area of electrodes for use as sensors for monitoring and controlling the process of electrolytic reduction of aluminum.

All primary aluminum extraction is done by electrolysis. In the Hall-Heroult process which predominates in the industry, aluminum oxide is dissolved in molten cryolite, $Na_3AlF_6$, which serves as the electrolyte. Aluminum oxide is decomposed into molten aluminum and carbon dioxide gas by the passage of electric current through the melt. A second electrolytic process involves the electrolysis of aluminum chloride dissolved in a solution of alkali chlorides, typically sodium chloride and lithium chloride. Aluminum chloride is decomposed into molten aluminum and chlorine gas by the passage of electric current through the melt.

Control of the electrochemical process requires the use of a reference electrode, a device in which a constant electrical potential (voltage) is established through the maintenance of thermodynamic equilibrium between chemically reacting species. A reference electrode can be thought of as an electrochemical probe or sensor. The reference electrode facilitates measurement of the concentration of aluminum in the bath and overvoltages at either the anode or cathode.

Prior art aluminum reference electrodes have not been able to provide a stable, drift-free output voltage. Prior art reference electrodes include gas electrodes; oxide electrodes ($Fe_2O_3$; $Fe_3O_4$; $Cr_2O_3$; $SnO_2$); metal electrodes (aluminum; Fe-Al, Pt-Al, or Pb-Na alloys; Pt, W); and liquid junction electrodes.

As described by K. Grjotheim et al. in *Aluminium Electrolysis*, 2nd ed., 195–206 (Aluminum-Verlag Dusseldorf FRG 1982), gas electrodes have problems with wear and lack of stability. Oxide electrodes are also unstable, possibly due to corrosion or the semiconducting nature of the oxides. Liquid junction electrodes require connection of the two half-cells by a diaphragm or salt bridge. Difficulties in finding a suitable diaphragm or salt bridge have restricted their use in cryolite melts. Further, mixing of the two melts continues to be a problem regardless of the material used to separate the half-cells.

An electrode comprising a molten salt and aluminum was first introduced by P. Drossbach in *Z. Elektrochem.*, Vol. 42, 65 (1936). A common type consists of a thin-walled tube of sintered alumina or boron nitride (BN) containing a molten aluminum pool covered with molten salt (cryolite). Another type provides access to the electrode through a small hole in the tube. Electrical contact with the electrode is by means of a platinum, tantalum or tungsten wire. As with the other prior art reference electrodes, reaction between the wire and the salt causes instability. Attempts to make electrical contact with the molten aluminum without also making contact with the molten salt have failed. Since the salt melt is not only highly corrosive but has great capillarity, the choice of materials for insulating the lead wire to the aluminum pool is limited. The salt melt eventually penetrates the lead insulator and shorts the lead wire to the salt. After shorting occurs, a mixed potential is established, and the voltage of the reference electrode becomes unstable.

It is therefore an object of the present invention to provide a reference electrode that generates a stable, drift-free output voltage and is thus useful for process control of aluminum extraction.

It is another object of the invention to provide a reference electrode useful in highly corrosive melts for advanced electrochemical analysis techniques, such as cyclic voltammetry.

It is a further object of the invention to provide an aluminum reference electrode that is useful in the analysis of refractory solids.

It is a still further object of the invention to provide a reference electrode useful in the conduction of corrosion tests in molten fluorides.

SUMMARY OF THE INVENTION

The present invention is a stable reference electrode for sensing the concentrations of metals in the electrochemical processing of metals including aluminum, the alkali metals, the alkaline earth metals, the rare earths, germanium, silicon, tin, zinc, antimony, gallium, indium, and thallium. An example is an aluminum reference electrode comprising: (1) an electrode consisting of a molten pool of aluminum or aluminum alloy; (2) an electrolyte consisting of a molten salt solution containing aluminum ions which equilibrate with aluminum metal to establish the potential or emf of $Al = Al^{3+} + 3e^-$; 3) a solid lead wire to make electrical contact with the metal pool; and (4) a container for separation of the electrode, electrolyte and lead wire from the cryolite bath that is being "probed".

The electrolyte of the reference electrode or "reference solution" preferably makes electrical contact with the electrolyte of the cell through a capillary, either a single small hole running through the container wall or, more preferably, by means of a porous plug e.g. sintered boron nitride (non-pyrolytic). At a minimum, the electrolytes must make contact. In the case where the electrolyte solution in the cell is different from the reference solution, the path must be very tortuous so that the two melts do not mix but instead establish a stable liquid junction.

In the preferred embodiment of the Hall cell aluminum reference electrode, the reference solution comprises cryolite, $Na_3AlF_6$, which has been diluted with a compound such as strontium fluoride or barium fluoride to increase the density of the reference solution to a value exceeding that of the aluminum. This change in density of the reference solution causes the aluminum to float on the surface of the molten salt. As a result, the electrically connecting means, such as a wire of tantalum, tungsten, titanium boride, or graphite, is not exposed to the corrosive salt. The same effect may be achieved by diluting the aluminum pool with a substance that is less electrochemically active and of a lower density than the aluminum whereby the density of the molten metal solution so formed is decreased to a value lower than that of the molten salt.

The same principle may be used to manufacture reference electrodes for sensing the concentrations of other metals in aluminum cells and for use in electrochemical processing of the same metals. Examples are the alkali metals, alkaline earth metals, the rare earths, germanium, silicon, tin, zinc, antimony, gallium, indium, and thallium. The choice of metal is governed by the following criteria: (1) the metal or metal alloy must be molten at the operating temperature of the cell or at the temperature of the electrolyte to be studied; and (2) the electrochemical activity must be such that the electrical potential established is for the equilibrium of the metal with its ions.

BRIEF DESCRIPTION OF THE DRAWING

FIG. 1 is a perspective view of laboratory-scale Hall cell containing a reference electrode according to the present invention.

DETAILED DESCRIPTION OF THE INVENTION

The present invention is a stable reference electrode exemplified by a Hall cell aluminum reference electrode wherein the molten aluminum pool "floats" on top of the reference solution. The density of the reference solution is altered by the addition of substances, such as $SrF_2$ or $BaF_2$, that increase the density of the electrolyte, usually $Na_3AlF_6$. The same effect may be achieved by diluting the aluminum with substances that decrease the density of the aluminum to below that of the reference solution. The stability of the electrode is increased by inverting the naturally encountered positions of the aluminum and reference solution to thereby eliminate mixed potentials.

Increased stability is derived from the lack of contact between the electrolyte and the lead wire. The problem with contact between the lead wire and the electrolyte is that the lead wire establishes an equilibrium of its own with the electrolyte. For example, tungsten will partially dissolve in cryolite and produce a tungsten/tungsten ion equilibrium, which in turn produces a voltage which is superimposed on the voltage of the aluminum-/aluminum ion equilibrium. The result is called a "mixed potential". The present reference electrode completely eliminates the problem of mixed potentials.

The reference electrode can be used in the electrochemical processing of metals other than aluminum. The choice of metal is governed by: (1) the metal or alloy must be molten at the cell operating temperature or at "the temperature of the electrolyte to be studied" and (2) electrochemical activity must be such that the electrical potential or emf established is for the equilibrium of the metal with its ions. It is not necessary that the melting point of the pure metal be less than the temperature of the electrolyte to be studied so long as the melting point of the alloy is lower than the temperature of the electrolyte. Using these criteria, the reference electrode can be used not only in aluminum electrolysis cells but also in melts in which oxides or other compounds or both are dissolved for chemical analysis. The reference electrode can also be used to sense the concentration of a specific metal ion during the electrochemical processing of metals such as alkali metals, alkaline earth metals, rare earths, germanium, silicon, tin, zinc, antimony, gallium, indium, and thallium.

The reference electrode is particularly useful in Hall-Heroult cells, where process control is improved through the use of the electrode in on-line determinations of the chemical composition of the bath and measurement of overvoltages at the anode or cathode.

The composition of the reference solution is determined both by the electrochemistry of the metal whose activity is to be measured and by the composition of the electrolyte under study. For example, aluminum oxide dissolved in cryolite, $Na_3AlF_6$, is used as the electrolyte in the Hall cell reduction of aluminum. Thus, the melt in an aluminum reference electrode for use in Hall cells is based on cryolite, $Na_3AlF_6$. In contrast, aluminum chloride dissolved in a supporting electrolyte such as a solution of sodium chloride and lithium chloride is used as the electrolyte in a second electrolytic reduction process for aluminum. Thus, the melt in an aluminum reference electrode for use in the second system is based on aluminum chloride dissolved in the same supporting electrolyte.

The lead wire must be a solid, constructed of a material that is (1) chemically stable in the molten metal pool and (2) an electronic conductor, for example, a metal or a conductive ceramic such as titanium diboride. Other materials will also serve this purpose.

The outer wall of the electrode must be constructed of a material that is (1) solid, (2) chemically stable in contact with the cryolite of the electrolysis cell, the electrolyte of the reference electrode, and the molten aluminum or aluminum alloy pool, and (3) dielectric, i.e. not an electronic conductor such as the noble metals, graphite, or titanium diboride. The reference solution and molten metal are contained by the outer wall formed of a material selected on the basis of the operating temperature of the process and the chemical reactivities of the species that it contacts. The material should be an electrical insulator, resistant to corrosion in the electrolyte solution, and sufficiently porous to allow ionic conductance between the electrolyte solution and reference solution. Sintered boron nitride, magnesium oxide, zirconium nitride, silicon nitride, silicon oxynitride, alumina, aluminum oxide, silica, aluminum silicate minerals, and fused quartz glass with a capillary tube are acceptable materials for chloride melts. Sintered boron nitride is the preferred material for fluorides, including cryolite. Other acceptable materials include magnesium oxide, zirconium oxide, silicon nitride and silicon oxynitride, although these materials may be attacked by the fluoride.

In one embodiment of a Hall cell aluminum reference electrode according to the present invention, the density of the aluminum is decreased to a value below the density of the reference solution. Selection of the diluent must take into consideration not only density but melting point of the alloy and relative electrochemical activity of the aluminum and diluent. Examples of useful diluents include the alkali metals, which are all less dense than aluminum: lithium (0.525 g/cm$^3$ at 181° C.), sodium (0.927 g/cm$^3$ at 97° C.), potassium (0.827 g/cm$^3$ at 64° C.), rubidium (1.437 g/cm$^3$ at 39° C.), cesium (1.854 g/cm$^3$ at 29° C.), and francium (2.35 g/cm$^3$ at 18° C.); alkaline earth metals: magnesium (1.59 g/cm$^3$ at 651° C.) and calcium (1.365 g/cm$^3$ at 865° C.); and beryllium (1.69 g/cm$^3$ at 1283° C.). Binary or multicomponent solutions of these metals, or combinations thereof, with aluminum can be selected to produce a molten aluminum alloy that is less dense than cryolite wherein only the aluminum is electrochemically active. Since the alkali metals may be volatile or may react with the gas atmosphere above the metal pool under the electrode operating conditions, it may be necessary to reduce their vapor pressure or minimize the concentration of the alkali metal.

It is not necessary to alter the density to the point at which the aluminum completely covers the reference solution. A wire of molybdenum or tungsten can be used when the aluminum pool does not float quite all the way to the top of the salt solution. The aluminum will wet the wire and protect it from the surrounding salt solution.

In a second embodiment of a Hall cell aluminum reference electrode according to the present invention, the density of the reference solution is increased to a value greater than the density of the aluminum. Additives to the reference solution in the Hall cell aluminum reference electrode that increase the density at 960° C. include alkaline earth fluorides including $CaF_2$, $BaF_2$, $SrF_2$, $MgF_2$, and $RaF_2$; and lanthanide fluorides including $LaF_3$ and $CeF_3$, and actinide fluorides including $ThF_4$. Solutions of 25 to 30 weight percent $SrF_2$ and $BaF_2$ are preferred to increase the density of $Na_3AlF_6$ to the point at which molten aluminum floats on it. $MgF_2$ has the least effect on the density and may interfere with measurements due to the electrochemical activity of the Mg. Empirically, aluminum floats on 30 weight % $SrF_2$ or $BaF_2$ in $Na_3AlF_6$ at 960° C.

In an embodiment of an aluminum reference electrode for use in aluminum chloride cells, the density of the reference electrode is increased to a value greater than the density of aluminum. Examples of additives to the reference solution in the aluminum reference electrode that increase the density at 960° C. include the alkaline earth chlorides with the exception of $MgCl_2$, the lanthanide chlorides and the actinide chlorides.

An example of a bench scale aluminum Hall-Heroult Cell using an aluminum reference electrode according to the present invention is shown in FIG. 1. The laboratory scale cell can pass current to make aluminum metal at temperatures and current densities similar to those encountered in industry. However, the intense electromagnetic fields encountered in industrial cells are not duplicated in the laboratory scale cell. The cell 10 consists of an $Al_2O_3$ crucible 12 filled with electrolyte 14 and aluminum 15 into which a cathode current lead 16 and anode 18 and anode specimen holder 19 are inserted. The crucible 12 could also be formed of graphite. The electrolyte 14, $Na_3AlF_6$, becomes molten when the crucible 12 is heated to approximately 960° C. The length of the electrodes 16, 18 can be varied.

The cathode wire 16 is surrounded by a boron nitride insulator 20. The wire 16 and Al pool 15 together act as the cathode. The cell 10 contains a boron nitride spacer 21 and is covered by a cap 22.

The reference electrode 24 consists of a tungsten wire 26, a pool 28 of molten aluminum, and a reference solution 30. The reference solution 30, consisting of the cell electrolyte with 30% $BaF_2$, is separated from the cell electrolyte 14 by a hot pressed BN container 32. The reference electrode 24 is covered by a gas tight seal 34.

In another embodiment of the Hall cell aluminum reference electrode, the reference solution comprises 30 weight % $SrF_2$ in $Na_3AlF_6$. The electrolyte 14 comprises 72.52 weight % $Na_3AlF_6$, 16.48 weight % $AlF_3$, 7.00 weight % $Al_2O_3$ and 4.00 weight % $CaF_2$. $AlF_3$ is added to adjust the starting bath ratio of $AlF_3$:NaF to 1.5:1. The electrolyte temperature is maintained at 960° C. in a resistance heated furnace. Temperature is measured with a Pt-13% Rh versus Pt thermocouple.

The disclosed reference electrode, alone or in conjunction with another electrode, is useful in determining the relative concentrations of the various components of the electrolyte. For example, aluminum oxide concentration can be determined by measuring voltage between a Hall cell aluminum reference electrode and an electrode consisting of oxygen gas at a fixed known pressure flushing over a platinum wire. Sodium fluoride concentration can be determined by measuring voltage between a sodium reference electrode constructed according to the present invention and an electrode consisting of $F_2$ gas at a fixed known pressure flushing over a platinum wire. Lithium fluoride may be measured using the same method as for sodium fluoride.

Method for determination of alumina (aluminum oxide) concentration in the Hall cell electrolyte or any molten salt containing alumina The aluminum reference electrode is immersed in the Hall cell electrolyte, consisting of the molten salt under study. An oxygen electrode is immersed in the same Hall cell electrolyte. A simple oxygen electrode is a platinum wire flushed with oxygen gas at a controlled pressure.

The difference in electrical potential (voltage) between the aluminum and oxygen electrodes is measured at open circuit. The result is the voltage associated with the formation of alumina in the melt at that temperature. Using the Nernst equation, the chemical potential and the concentration of alumina are calculated.

Nernst Equation for this case:
$$E = E° - \frac{RT}{6F} \ln a_{Al_2O_3}$$

wherein:
E is the measured open circuit potential between Al and $O_2$ electrodes
E° is the standard potential calculated from tabulated thermochemical data
R is the gas constant
T is the bath temperature
F is the Faraday constant
$a_{Al_2O_3}$ is the activity or chemical potential of $Al_2O_3$ in the bath under the conditions of measurement, i.e. composition and temperature Method for the determination of the bath ratio for a Hall cell electrolyte or any other molten salt electrolyte The bath ratio is defined as the mass ratio of sodium fluoride to aluminum fluoride. Industrial Hall cells operate at bath ratios of 1 to 1.5. The performance of the cell is strongly dependent upon the bath ratio.

The aluminum reference electrode is immersed in the melt under study. A fluorine electrode and a sodium electrode are immersed in the same melt. The difference in electrical potential between the aluminum and fluorine electrodes can be converted using the Nernst equation into a measure of the concentration of aluminum fluoride in the melt.

$$E_1 = E° - \frac{RT}{3F} \ln a_{AlF_3}$$

The difference in electrical potential between the sodium and fluorine electrodes can be converted using the Nernst equation into a measure of the concentration of sodium fluoride in the melt.

$$E_2 = E° - \frac{RT}{F} \ln a_{NaF}$$

With these two data, the ratio of sodium fluoride to aluminum fluoride can be calculated. It is possible to ratio the voltages and determine bath ratio electronically in real time.

EXAMPLE 1

Long term stability of the Hall cell aluminum reference electrode of the present invention A Hall cell aluminum reference electrode, similar to the one shown in FIG. 1, was used in the following example to demonstrate the stability of the reference electrode against short term fluctuations.

Oxygen evolution on a platinum anode in a Hall cell tested. The cell voltage was fixed at 2.65 volts. The variation in cell current was followed while measuring the potential between the anode and the reference electrode. After 40 minutes, the cell current had decreased from 770 mA to 720 mA, while the anode versus reference voltage had increased only 25 millivolts from 2.415 volts to 2.440 volts. Current fluctuations were typically on the order of ±10 milliamps or ±1.5% while fluctuations in anode versus reference voltage were below the limit of detection of the chart recorder at the scale settings, in this case ±5 millivolts or ±0.2%.

The results demonstrate that the reference electrode is stable against short term fluctuations. The observed long term drift is consistent with cell performance as a whole over the same time period. Some change in anode to reference potential is expected in view of the change in cell current which is attributed to compositional changes in the cell bath. In this example, the $Al_2O_3$ concentration decreased over time.

EXAMPLE 2

Polarization test of the aluminum reference electrode of the present invention

An aluminum reference electrode, similar to the one shown in FIG. 1, with an aluminum pool floating on 30 weight % $BaF_2$ in cryolite as the reference solution and a solid tungsten lead wire, was placed in a cryolite bath at a temperature of 960° C. The cell test was conducted on a graphite anode. Results are shown in Table I.

TABLE I

| Time (Minutes) | Anode Versus Reference Electrode (Volts) |
|---|---|
| 0 | 0.663 |
| 17 | 0.657 |
| 85 | 0.656 |
| 200 | 0.648 |
| 204 | 0.653 |
| 208 | 0.643 |
| 240 | 0.639 |

Time is measured from the instant at which the tungsten lead wire is immersed in the floating aluminum pool. After 200 minutes, the reference electrode is polarized by passing a current of 50 milliamps, which is very high for such a test, between the reference electrode and a counterelectrode in the cell for a period of 3 seconds. After only 4 minutes, the reference electrode returned to its rest potential. The reference electrode was then polarized again. A current of 50 milliamps is made to pass in the opposite direction from the previous polarization. After only 4 minutes, the reference electrode again returned to its rest potential.

After 4 hours of cell exposure, the change in anode versus reference potential was 24 millivolts. The fact that the reference potential returned to its rest potential after each polarization demonstrates that the potential is the result of a stable electrochemical equilibrium. The kinetics of approach to equilibrium in this reference electrode are very favorable, as evidenced by the rapid return to the rest potential. A small deviation can be attributed to compositional changes in the cell and reference electrolytes caused by the polarization itself.

The reference electrode according to the present invention also facilitates the adaptation of advanced electrochemical analysis techniques, such as cyclic voltammetry, for use in highly corrosive melts such as molten fluorides. These melts are useful not only for aluminum reduction but also for dissolving refractory materials which can then be analyzed for their chemical composition. For example, a multi-component oxide, such as a complex mineral, which is sparingly soluble in water or aqueous acid solution may be readily soluble in a molten fluoride solution. With the aid of the reference electrode described herein it is possible to conduct electro-analytical studies of the composition of the mineral. Further, the reference electrode allows proper scientific corrosion tests to be performed in molten fluorides. These tests are impossible to conduct without a reference electrode.

Fused salts are a technologically important class of liquids because they do not have some of the limitations of aqueous solutions. Specifically, the range of decomposition potentials for solutes is greater in molten salts than in aqueous solutions. This allows the electrodeposition of highly electropositive metals, the preparation of very electronegative elements such as fluorine, high-temperature electrochemistry (200° C. to 1500° C.), and electrochemical synthesis of many inorganic compounds such as oxides, nitrides, carbides and other materials. Up until now, the degree of electrochemical characterization, particularly in molten fluorides, has been limited by the lack of a stable reference electrode.

Although this invention has been described with reference to specific embodiments, it is understood that modifications and variations of the compositions and methods of processing may occur to those skilled in the art. It is intended that all such modifications and variations be included within the scope of the appended claims.

We claim:

1. A reference electrode for measuring or controlling the electrical potential of an electrochemical reaction in a cell comprising:
   an electrochemically active molten metal pool, wherein the electrical potential is established by the equilibrium of the metal with ions of said metal produced by the electrochemical reaction,
   a barrier permeable to the metal ions produced in the cell,
   a reference solution comprising a molten salt solution and the metal ions, and
   conductive means electrically connecting the metal pool to means for measuring electrical potential,
   wherein the permeable barrier surrounds and contains the reference solution and metal pool, and
   wherein the density of the reference solution is more than the density of the metal so as to lie below the molten metal pool at the operating temperature of the cell and the metal pool contacts the electrically conductive means from above to the exclusion of the reference solution.

2. The reference electrode of claim 1 wherein the reference solution further comprises one or more components to increase the density of said reference solution to a value greater than the density of said metal.

3. The reference electrode of claim 2 wherein said reference solution comprises components whose relative electrochemical activities are such that the electrical potential is determined by the equilibrium of said metal and metal ions to be measured.

4. The reference electrode of claim 3 wherein said reference solution is $Na_3AlF_6$ diluted with one or more compounds selected from the group consisting of alkaline earth fluorides, lanthanide fluorides, and actinide fluorides.

5. The reference electrode of claim 3 wherein said reference solution is aluminum chloride-alkali chloride diluted with one or more compounds selected from the group consisting of calcium chloride, strontium chloride, barium chloride, radium chloride, lanthanide chlorides, and actinide chlorides.

6. The reference electrode of claim 1 wherein said metal is aluminum.

7. The reference electrode of claim 6 wherein said metal pool is diluted with a second metal to decrease the density of said metal pool to a density less than the density of said reference solution, wherein the electrochemical activity of said diluted metal pool is such that the electrical potential is for the equilibrium of the first metal with ions of the first metal.

8. The reference electrode of claim 7 wherein the metal pool is diluted with one or more compounds selected from the group consisting of the alkali metals, magnesium, calcium, and beryllium.

9. The reference electrode of claim 1 wherein said metal is selected from the group consisting of the alkali metals, the alkaline earth metals, the rare earths, germanium, silicon, tin, zinc, antimony, gallium, indium and thallium.

10. The reference electrode of claim 9 wherein said metal pool is diluted with a second metal pool to decrease the density of said metal pool to a density less than the density of said reference solution, wherein the electrochemical activity of said diluted metal pool is such that the electrical potential is for the equilibrium of said first metal with ions of the first metal.

11. The reference electrode of claim 1 wherein the electrically conductive means comprises a solid lead wire consisting of a material chemically and electrochemically stable in said metal pool.

12. The reference electrode of claim 11 wherein said material is a metal.

13. The reference electrode of claim 11 wherein said material is an electronically conducting ceramic.

14. The reference electrode of claim 1 wherein said permeable barrier comprises a solid dielectric material chemically stable when immersed in the electrolyte of the electrochemical cell.

15. A method for measuring or controlling the electrical potential of an electrochemical cell or reaction comprising:
(a) constructing a reference electrode comprising an electrochemically active metal, wherein the electrical potential is established by the equilibrium of the metal with ions of the metal produced by the electrochemical reaction and wherein the metal forms a molten pool at the operating temperature of the electrochemical reaction,
a barrier permeable to the metal ions produced in the cell,
a reference solution comprising a molten salt solution and the metal ions,
electrically conductive means connecting the metal pool to means for measuring electrical potential,
wherein the barrier surrounds and contains the reference solution and metal pool;
(b) altering the relative density of the metal pool and the reference solution so that the metal pool is less dense at the operating temperature of the cell than the reference solution and contacts the electrically conductive means from above to the exclusion of the reference solution;
(c) connecting the conductive means to a means for measuring electrical potential; and
(d) placing the reference electrode in an electrolyte of the electrochemical cell.

16. The method of claim 15 further comprising selecting the components of the metal pool from the group consisting of aluminum, the alkali metals, the alkaline earth metals, the rare earths, germanium, silicon, tin, zinc, antimony, indium, gallium and thallium.

17. The method of claim 16 comprising:
(a) constructing a reference electrode comprising an aluminum pool,
a barrier permeable to aluminum ions,
a reference solution comprising $Na_3AlF_6$,
solid, electrically conductive means connecting the metal pool to a means for measuring electrical potential,
wherein the barrier surrounds and contains the $Na_3AlF_6$ reference solution and aluminum pool; and,
(b) altering the relative density of the aluminum pool and the $Na_3AlF_6$ reference solution so the aluminum contacts the electrically conductive means to the exclusion of the reference solution.

18. The method of claim 16 comprising:
(a) constructing a reference electrode comprising an aluminum pool
a barrier permeable to aluminum ions,
a reference solution comprising aluminum chloride,
solid, electrically conductive means connecting the metal pool to a means for measuring electrical potential,
wherein the barrier surrounds and contains the aluminum chloride reference solution and aluminum pool;
(b) altering the relative density of the aluminum pool and the aluminum chloride reference solution so the aluminum contacts the electrically conductive means to the exclusion of the reference solution;
(c) connecting the conductive means to a means for measuring electrical potential; and
(d) placing the reference electrode in the electrolyte of the electrochemical cell.

* * * * *